United States Patent [19]

Saaski et al.

[11] Patent Number: 4,983,824
[45] Date of Patent: Jan. 8, 1991

[54] OPTICALLY RESONANT SENSOR WITH INCREASED MONOTONIC RANGE

[75] Inventors: Elric W. Saaski, Bothell; Dale M. Lawrence, Lynnwood, both of Wash.

[73] Assignee: MetriCor Inc., Woodinville, Wash.

[21] Appl. No.: 376,789

[22] Filed: Jul. 6, 1989

[51] Int. Cl.$^5$ .............................. H01J 5/16; G01D 5/34
[52] U.S. Cl. ............................ 250/227.27; 250/231.19; 250/227.23
[58] Field of Search ............... 250/231 P, 231 R, 227, 250/231.19, 231.10, 227.21, 227.23, 227.18, 227.19, 227.27; 73/705, 715, 717, 862.58, 862.59, 862.62, 722, 800; 356/357, 345, 358

[56] References Cited

U.S. PATENT DOCUMENTS

| | | | |
|---|---|---|---|
| 3,387,494 | 6/1968 | Golay | 73/705 |
| 4,473,747 | 9/1984 | Brogardh et al. | 250/231 P |
| 4,588,886 | 5/1986 | Snider | 250/231 P |
| 4,617,608 | 10/1986 | Blonder et al. | 73/705 |
| 4,678,902 | 7/1987 | Perlin | 250/231 P |
| 4,682,500 | 7/1987 | Uda | 73/705 |
| 4,757,194 | 7/1988 | Simms | 250/231 P |

Primary Examiner—Davis L. Willis
Assistant Examiner—Michael Messinger
Attorney, Agent, or Firm—K. McNeill Taylor, Jr.

[57] ABSTRACT

A variable gap optical sensor device with a pair of opposed reflective surfaces and having a periodic response function. The sensor includes stiffening means or limiting means intermediate the reflective surfaces to diminish the potential variation in the gap between the reflective surfaces and thereby increase the monotonic range of the periodic response function, resulting in a dual stage sensor response function with a second stage having an increased period.

26 Claims, 4 Drawing Sheets (PRIOR ART)
Fig. 1

OPTICALLY RESONANT SENSOR WITH INCREASED MONOTONIC RANGE

BACKGROUND OF THE INVENTION

This invention relates to optically resonant sensors with periodic response functions.

Optically resonant structures are used in sensor devices that monitor pressure, temperature, refractive index, gas density, pH and other parameters. Typical sensors are disclosed in U.S. Pat. Nos. 4,678,904 and 4,778,987, which are both entitled Optical Measuring Device Using a Spectral Modulation Sensor Having an Optically Resonant Structure, and which are both assigned to the assignee of the present invention.

For some of these optically resonant sensors, for example pressure sensors and refractive index sensors, the sensor output or response function is periodic or cyclical. That is, the response function values may be the same for different values of the parameter being monitored. This results in sensor inaccuracy, especially at crossover points where the slope of the response function curve goes through zero from positive to negative or vice versa.

At these crossover points, even though the value of the sensed parameter is increasing or decreasing at a relatively constant rate, the change in value of the response function appears to slow down and then reverse itself, indicating that the direction of the change in value of the sensed parameter has also reversed, and thus giving an ambiguous and inaccurate measurement of the sensed parameter.

The range of accurate sensor operation is typically limited to regions of the periodic response function that are monotonic with respect to the parameter being measured. A monotonic function has the property of either never-decreasing or never increasing as the independent parameter being measured increases. For example, a sine function is monotonic between any adjacent maximum and minimum In conventional interferometric sensors, this problem results from the fact that the average gap width between the opposed reflective surfaces is generally several wavelengths deep, relative to the center wavelength of the light source being used to interrogate the sensor. This means that if the external parameter being monitored (e.g., pressure) is applied beyond the full-scale design limit, the sensor output will display a periodic response. This is an inherent property of any interferometric sensor operated at a maximum gap width in excess of approximately $\frac{1}{4}$ wavelength. Therefore, at some deflection in excess of approximately $\frac{1}{4}$ wavelength, an interferometric sensor will indicate a decreasing value for the parameter when in fact it is increasing. This issue is particularly important for non-fringe-counting interferometric devices with gap width in the undeformed state of less that about 30 μm.

One technique for mitigating this problem is described in the above-referenced U.S. Pat. No. 4,678,904 at col. 9, lines 7–23 and is based on the selection of appropriate sensor design and interrogating light. Another such technique is described at col. 12, lines 1–26 and is based on a ratiometric processing of the sensor output to yield a response function with a period that can approach twice the period of the amplitude of the sensor output light. Even when these techniques are applied, however, the response functions remain periodic the sensors are optimized but continue to give ambiguous readings at both extremes of their monotonic operating ranges.

The periodic nature of the sensor response function is not as critical for some applications as for others. For example, human blood pressure will not exceed about 300 mmHG except under highly unusual conditions. It is then only necessary to design diaphragm stiffness so that the output does not "double back" unless the pressure exceeds, perhaps, 400 mmHg.

However, in some industrial control situations, it is desirable to have a monotonic response for parameter values significantly greater than the full-scale amount.

Therefore, it is an object of this invention to extend the monotonic response range of sensors with periodic response functions.

It is another object of this invention to provide a sensor in which the multiple response cycle phenomena is inhibited, while at the same time providing a sensor design that results in a change in sensor operation when the parameter being measured goes outside the normal operating range of the sensor. In other words, it is an object of this invention to provide an increased monotonic response range and dual-range sensing. For example, in a pressure sensor device, if a transient condition occurs in which system pressure goes to 150% of full-scale and slowly rises, the sensor output according to the present invention indicates a pressure increasing at a different rate rather than an erroneous decreasing pressure.

It is a further object of the invention to increase the tolerance of the sensor beyond its normal operating range to a point that the system is unlikely to erroneously read in-range unless the sensor is subjected to unreasonably high values of the parameter being measured.

SUMMARY OF THE INVENTION

These and other objects are achieved in accordance with the invention which, in one aspect, relates to a variable gap optical sensor device with a periodic response function. The sensor device includes a pair of opposed reflective surfaces, at least one of said surfaces being flexible so that the gap width between the reflective surfaces can be varied, the gap in the undeformed state being no greater than 30 μm. The sensor device further includes an optical fiber mounted with respect to said opposed reflective surfaces so that light from the core of said fiber will be incident on at least a portion of said surfaces, and light reflected from said surfaces will be incident on said core. And, the sensor device includes stiffening means intermediate said opposed reflective surfaces, whereby the potential variation in said gap width is diminished, thereby increasing the monotonic range of said periodic response function.

In accordance with another aspect, the invention relates to an optically resonant sensor comprising a pair of opposed reflective surfaces and having a periodic response function, wherein the sensor includes stiffening means for at least one of said opposed reflective surfaces whereby a second stage of said response function is created with increased period and the operating range in which said response function is monotonic is increased.

In accordance with a further aspect, the invention relates to an optically resonant sensor device with a pair of opposed reflective surfaces which are interrogated with light to generate a response function that varies periodically as the distance between the opposed reflective surfaces varies monotonically in response to the parameter being sensed. The distance between the opposed reflective surfaces corresponds with the value of the parameter being monitored by the sensor. During operation of the sensor, there is a range of distances between said opposed reflective surfaces which corresponds with a selected monotonic region of a first stage of said periodic response function in which there is a unique one-to-one relation between the values of the response function and the monotonically varying distance between said opposed reflective surfaces. Said sensor device further comprises limiting means for altering the period of said periodic response function to increase the range of said distances in which said response function is periodic thereby creating a dual stage monotonic sensor response.

In accordance with yet another aspect of the invention, there is provided a a mechanical stop technique that extends the monotonic response range of deflecting diaphragm interferometric sensors.

DETAILED DESCRIPTION

Figure 1:
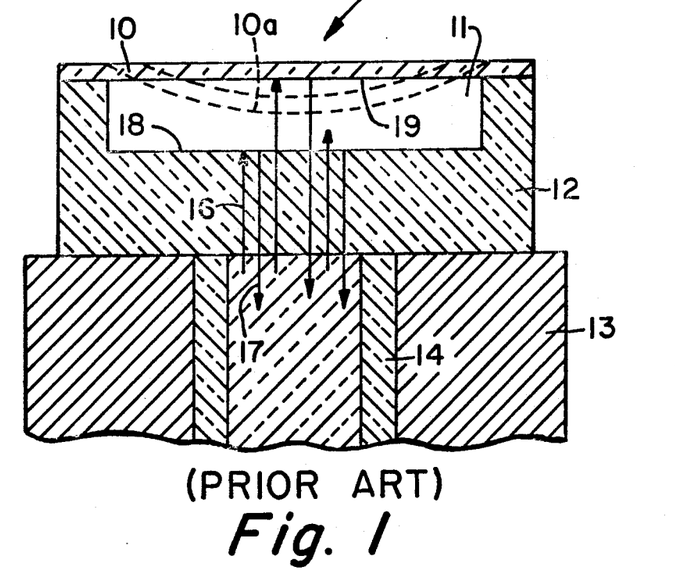
FIG. 1 illustrates an interferometric sensor with bowing diaphragm attached to an optical fiber.

FIG. 1 depicts in cross section an interferometric sensor 15 without the present invention. Sensor 15 includes bowing diaphragm 10 attached to transparent substrate 12 to form resonant cavity 11. Substrate 12 is attached to support pedestal 13 which positions optical fiber 14 to transmit input light 16 to cavity 11 and to receive returned light 17 from the cavity. Cavity 11 is typically a flat-bottomed pocket etched into a refractory glass substrate 12. Diaphragm 10 is typically a partially reflecting single crystal silicon. The depth of cavity 11 is typically 2 to 3 times the central wavelength of incident light 16. The two closely-spaced surfaces (i.e., inner surface 19 of diaphragm 10 and bottom surface 18 of cavity 11) form an optically resonant interferometer, reflecting light with an efficiency that depends on both wavelength and local cavity gap.

When sensor 15 is used as a pressure sensor, the shallow cavity 11 is evacuated and sealed with thin diaphragm 10. The diaphragm bows under pressure to the position indicated by 10a, and hence the cavity depth changes directly with applied pressure, modulating the spectrum of incident light 16 into returned light 17.

Figure 2:
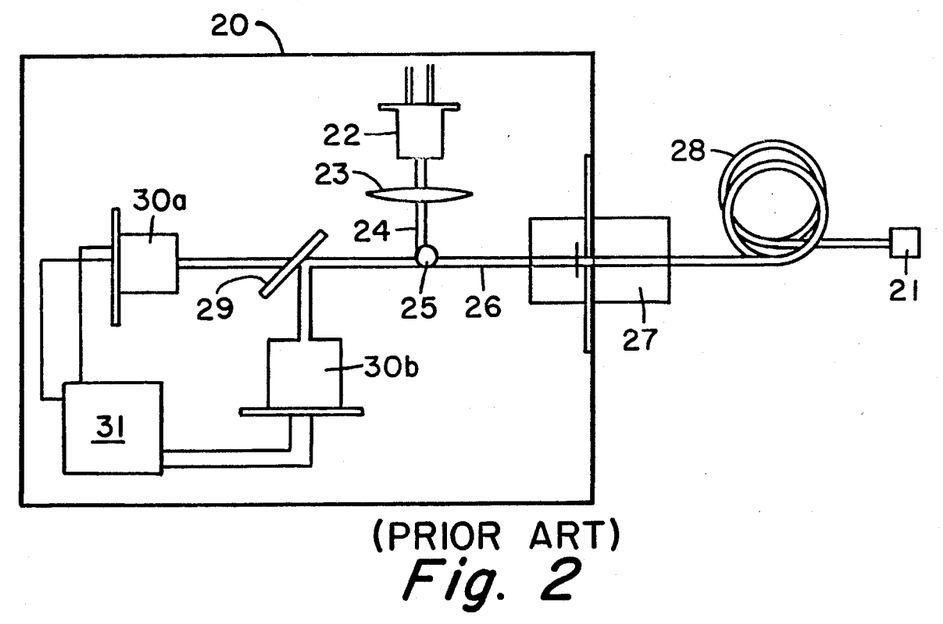
FIG. 2 is a schematic of an optical measuring instrument utilizing a ratiometric detection technique to interrogate an interferometric sensor.

FIG. 2 depicts an optical measuring instrument 20 utilizing a ratiometric detection technique to interrogate an interferometric sensor such as sensor 15 in FIG. 1. It may also be used to interrogate the inventive sensor device which will be described hereinafter. The ratiometric detection technique is described in detail in U.S. Pat. No. 4,678,904 which is assigned to the assignee of the present invention and which is incorporated herein by reference.

Figure 3:
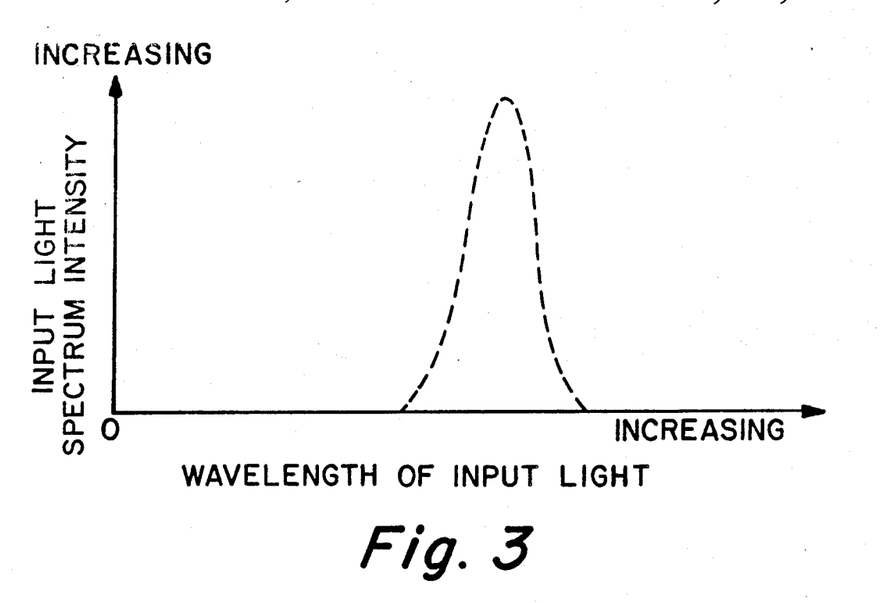
FIG. 3 is a graphic representation of an input light used in the optical measuring instrument of FIG. 2.

Optical measuring instrument 20 uses "micro-shifts" of reflectance spectrum of the sensor in sensor probe 21 with respect to the spectrum of the input light received from LED light source 22. In one embodiment depicted in FIG. 3, the input light is centered at a wavelength of 85 $\mu$m. As the effective depth of the sensor cavity varies (due to a change in the parameter being measured, for example, pressure), the cavity's reflectance spectrum shifts in wavelength. This spectral shift modulates the incoming LED spectrum, resulting in a new, skewed light spectrum returning to the receiver.

In the operation of optical measuring instrument 20, input light from LED source 22 is focused by lens means 23 onto lightguide 24 which is connected by coupler 25 to lightguide 26. The input light is transmitted through instrument bulkhead connector 27 and fiber cable 28 to sensor probe 21, which is positioned for monitoring the parameter being measured. The sensor within sensor probe 21 modulates the input light and returned light is generated as described in connection with FIG. 1. The returned light is transmitted through fiber cable 28 and instrument bulkhead connector 27 to fused coupler 25 where the returned light is directed toward optical beam splitter 29. In one embodiment, optical beam splitter 29 is a dichroic filter which divides the returning spectrum into long and short wavelength portions.

These wavelength portions are then converted into photocurrents using matched photodiodes 30a and 30b. The ratio of the two photocurrents is processed by electronics 31 to provide a measurement of the parameter being monitored. This ratio is proportional to the relative amount of light contained within the two wavebands and can be made monotonic relative to the parameter of interest over a range of operation of the sensor. Ratiometric detection provides advantages over simple amplitude-modulated signal recovery by providing first-order independence from system fluctuations caused by fiber bending, connector variations, and the like.

Figure 4:
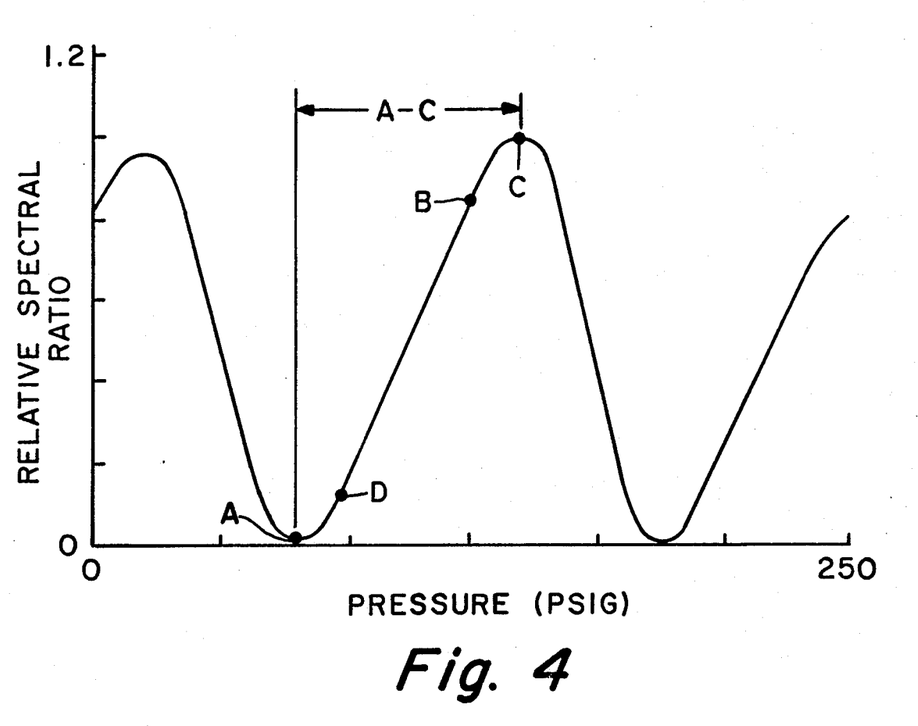
FIG. 4 is a graphic representation of the ratiometric response function of a typical interferometric sensor such as that depicted in FIG. 1.

FIG. 4 depicts the relative spectral ratio as a function of pressure as measured by the optical measuring instrument of FIG. 2 using a conventional interferometric sensor such as that depicted in FIG. 1. The relative spectral ratio varies in periodic sinusoidal fashion from 0 to 1 as the pressure varies from 0 to 250 psig. Typically, the monotonic response range of the sensor will be limited to the portion of the curve between points A and C. For pressures that generate spectral ratios outside this range, the optical measuring instrument of FIG. 2 will yield ambiguous, inaccurate results.

Figure 5:
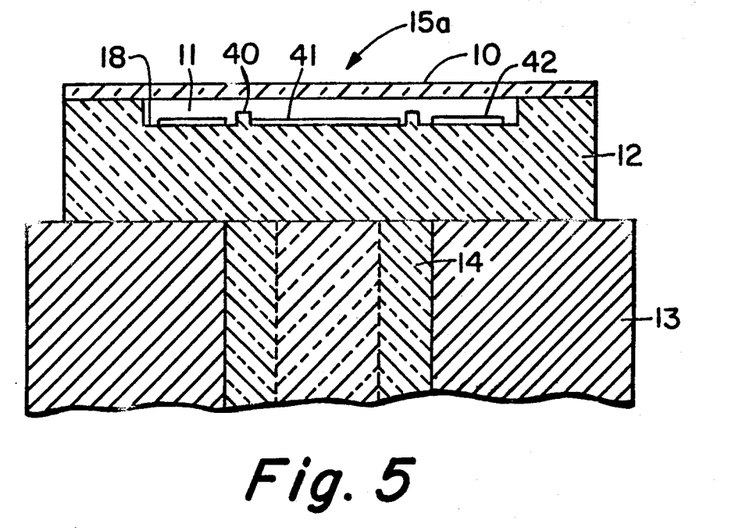
FIG. 5 illustrates an interferometric sensor in accordance with one embodiment of the invention.

The present invention dramatically mitigates this problem. A basic form of the invention is depicted in FIG. 5. In FIG. 5, sensor 15a has many of the features of sensor 15 of FIG. 1: diaphragm 10 which provides a flexible reflective surface, substrate 12, support pedestal 13 and optical fiber 14 with core and cladding. In addition, sensor 15a includes stiffening means or limiting means comprising raised annular stop ring 40 mounted on bottom surface 18 of cavity 11. The inside diameter of stop ring 40 defines a clear aperture approximately equal to that of optical fiber 14 so that it does not interfere with the optically active central resonator area. The ring is made by selective masking and etching steps added during the etching process in which cavity 11 is formed. For certain pressure sensor applications, getter ring 42 may be deposited on bottom surface 18 of cavity 11 to absorb residual gasses or outgassing after initial evacuation of cavity 11. Reflective layer 41 may be formed by successive depositions of a suitable material, e.g., titanium dioxide, to bottom surface 18 of cavity 11 to increase its reflectivity.

Up to a point, sensor 15a functions similarly to the conventional interferometric sensor 15 of FIG. 1. However, as diaphragm 10 deflects, it eventually comes into contact with stop ring 40. Incremental deflection of the diaphragm after contact is significantly retarded, and substantially greater diaphragm force is required to increment the photocurrent ratio: the diaphragm becomes substantially stiffer. Stiffness of such a mounted diaphragm is roughly proportional to the diaphragm diameter raised to the 4th power.

In one embodiment of the invention, a cylindrical cavity 11 with 350 $\mu$m outside diameter includes stop ring 40 with 125 $\mu$m inner diameter. This embodiment is appropriate when the diameter of the core of optical fiber 14 is 100 $\mu$m. Since the stiffness of a diaphragm is proportional to the fourth power of the unsupported diameter, the inherent stiffness increase is approximately $(350/125)^4 = 61.4$ times. The actual stiffness gain is somewhat less because stop ring 40 is a pivot-type joint whereas diaphragm 10 is mounted to the lip of substrate 12 in a fixed joint.

In any case, the deflection per unit force on diaphragm 10 is substantially reduced when the stop is engaged. Referring now to FIG. 4, this engagement is designed to occur slightly before full-scale deflection at a point below the apex of the ratiometric response curve, for example point B. Full-scale deflection denotes the deflection of the diaphragm at which the response function of the sensor is no longer monotonic. In FIG. 4, at point C, the relative spectral ratio goes through zero slope and begins to decrease. A typical design provides for stop engagement at a point 15% below the value of the response function that corresponds with full-scale deflection. With such a design rule, sensor 15a will have a substantial capability beyond its normal monotonic operating range before its response becomes non-monotonic. In addition, the sensor will behave in a monotonic fashion up to the point of full-scale deflection.

Figure 6:
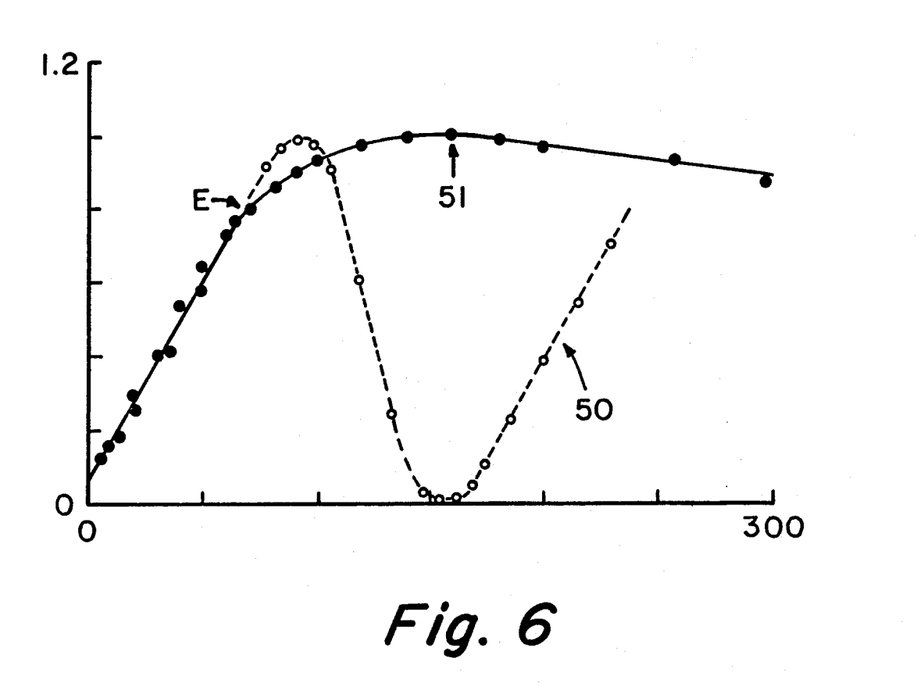
FIG. 6 is a graphic representation of the ratiometric response function of the invention compared with a response function similar to that depicted in FIG. 4.

The effect of stop ring 40 as measured by the optical measuring instrument of FIG. 2 is shown in FIG. 6. The sensor used to generate the response function depicted in FIG. 6 had a cavity diameter of 356 microns and a mean ring diameter of 148 microns. The cover was a thin membrane of single-crystal silicon. Sinusoidal curve 50 shows the sensor response function without a stop ring. Curve 51 shows the response function with a stop ring. E denotes the point of contact between the stop ring and the flexible diaphragm. The stop ring increased the monotonic range of the sensor from 130% of the deflection at point E to 250%. In addition, the stop ring increased the ratio at which the optical response erroneously returned to an in-range reading from 160% of the deflection at point E to 580%.

Figure 7:
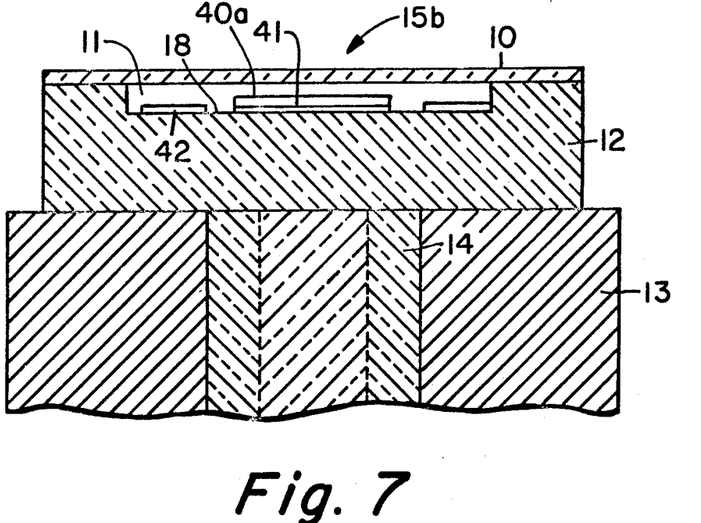
FIG. 7 illustrates an interferometric sensor in accordance with a secondembodiment of the invention.

A second embodiment of the invention is depicted in FIG. 7, which includes solid stop 40a made of a transparent rigid media. Solid stop 40a acts as a stiffening means or limiting means on diaphragm 10, in similar fashion to raised annular stop ring 40. The primary function of this media is mechanical, although any additional optical properties must also be considered. For example, the material's index change with temperature may have an effect on sensor stability. In the most favorable of circumstances, it may be possible to tailor the sensor so that the stop's optical properties actually improve optical performance.

Figure 8:
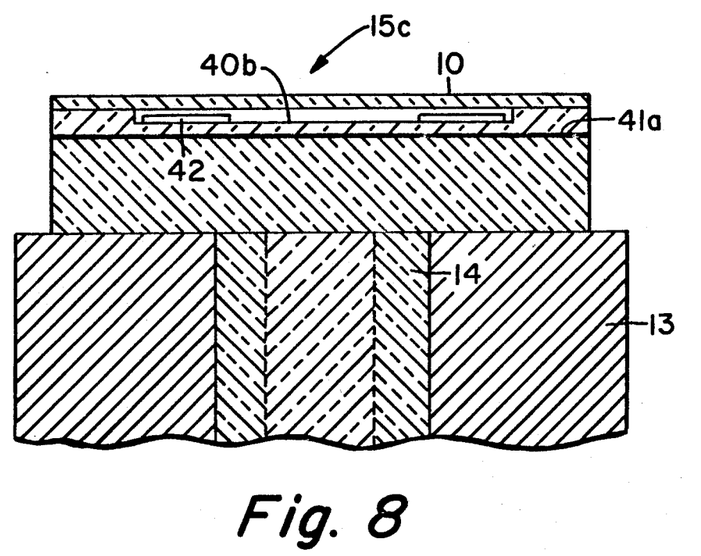
FIG. 8 illustrates an interferometric sensor in accordance with a third embodiment of the invention.

A third embodiment of the invention is depicted in FIG. 8. Solid stop 40b in FIG. 8 is made by first depositing successive layers of a suitable reflective material (e.g., titanium dioxide) to form cavity bottom reflecting film 41a and a thicker second film of a rigid transparent media which will form solid stop 40b. The second film is then etched to a depth appropriate for solid stop 40b, and diaphragm 10 is sealed onto its exposed face. The advantage of the alternative embodiment depicted in FIG. 8 is that an etching step can be used for processing the thick film while it would be much more difficult to remove excess media in the fabrication of the sensor depicted in FIG. 7.

The solid stop depicted in FIGS. 7 and 8 has several interesting features when compared to the ring stop. The solid stop contacts at the center of the sensor diaphragm first and increases in contact across the optically active central area as the force increases. This results in a very well-defined and 'hard' stop condition; however, it does not provide the gradual beyond range response that the ring does. On the other hand, the solid stop can be designed so that there is no possibility that the sensor deviates from monotonic behavior for any measured parameter.

The solid stop is more difficult to fabricate than the raised annular stop ring because of the need for a substantial (typically 1-2 microns) stop thickness. Sputtering is a deposition process of choice for generating this element. Suitable stop layers are silica, Pyrex glass, and aluminum oxide; other media may also be used.

A dual-range sensor can be made by designing the position of the stiffening means in the cavity so that it provides the desired increase in stiffness to produce a useful second range of measurements. For example, a pressure sensor designed to engage the stop described in connection with FIG. 5 at 50% of full-scale could have dual-ranges of 0 -12mmHg and 0-760 mmHg. Such a sensor could for example be used for vacuum process monitoring.

The manner in which optically resonant sensor 15a are made will now be described with particular reference to FIG. 5.

In order to reduce cost, it is preferred that a plurality of sensors 15a be produced simultaneously. By way of non-limiting example, it will be presumed that the optically resonant sensors 15a have cavities 11 which are 350 microns in diameter and 2.55 microns deep.

The starting point is, for example, a 7740 Pyrex glass wafer, both surfaces ground and polished to an optical finish, such as made by Vogelin Optical Co., Inc. of St. Paul, Minn. The glass wafer will form the substrates 12 of the sensors 15a.

The surfaces of the glass wafer are first cleaned by washing the glass wafer in hot, soapy water, rinsing it with clean water; etching and polishing it for one minute in a buffered HF solution composed of four parts of a mixture of 3 ml of water and 2 g $NH_3F$ plus 1 part 48% HF solution; rinsing it again, and then baking it at 300°, for ½ hour.

Using a conventional vacuum deposition process, a layer of chrome 200 Angstroms thick is then deposited on the glass wafer. This chrome provides a good adhesion surface for the subsequent application of photoresist to the glass wafer.

Photoresist, such as Microposit 1400-27 photoresist made by the Shipley Company, located in Newton, Mass., is then spin coated on the chrome surface of the glass wafer at 3000 rpm; after which the coated glass wafer is based at 90° C. for ½ hour.

Using conventional techniques, a photographic mask is then prepared having an array of concentric annular ring structures. The outermost ring diameter is equal to the desired diameter of the cavities 11, here 350 microns for example, and has an I.D. of 210 microns. The center ring is a disc of 150 microns diameter. The mask is aligned with the photoresist coated surface of the glass wafer; and the mask and glass wafer assembly is then exposed. The exposed coated glass wafer is then developed with photoresist developer, such as Microposit 351CD-23 developer made by the Shipley Company; rinsed in water; and dried.

As a result, an unprotected outer annular ring and inner disc are generated with a protected ring of 210 microns O.D. and 150 microns I.D. between them. The chrome within the unprotected areas in the photoresist is lifted off with a chrome etch solution composed of one part HCL and one part glycerin.

The areas of unprotected glass on the glass wafer are then etched for about 35 minutes at 69° F. with said buffered HF solution to produce the cavities 11 which are 2.05 microns deep, at this step in the process. Even though the bottoms 18 of the cavities 11 are formed by chemical etching, they are still flat enough to form an adequate reflective surface for the optically resonant sensor. Next the photoresist is removed with photoresist remover such as Microposit 1165 photoresist remover made by the Shipley Company and rinsed in water and dried.

Using conventional techniques, a photographic mask is then prepared having an array of disks of a diameter equal to the desired outside diameter of the cavities 11, here 350 microns. The mask is aligned with the photoresist coated surface of the previously etched glass wafer and the mask and glass wafer assembly is then exposed. The exposed coated glass wafer is then developed with photoresist developer, such as Microposit 351-CD-23 developer made by the Shipley Company, rinsed in water; and dried.

As a result, unprotected disks 350 microns in diameter in the photoresist are left on the glass wafer. The chrome within the unprotected disks in the photoresist, which now after the first etching only exist on the top of the raised annular stop rings 40, is lifted off with a chrome etch solution composed of one part HCL and one part glycerin, leaving the whole 350 micron cavity area unprotected.

These unprotected cavities, with internal elevated stop ring areas, are further etched for an additional five minutes at 69° F. with said buffered HF solution to produce cavities 11 which are about 2.55 microns deep with the annular stop ring elevated 2.05 microns above the cavity bottom.

Using conventional vacuum deposition techniques, a layer 41 of titanium dioxide 200 Angstroms thick is then deposited on the bottom 18 of each cavity 11 to increase the reflectivity of the bottoms 18 of the cavities 11. This increases the intensity of the modulation of the output light of the optically resonant sensors.

Thereafter, the remaining photoresist and chrome on the glass wafer are removed with acetone and with said chrome etch solution respectively, after which the glass wafer is washed in water and air dried.

Diaphragms 10 for cavities 11 of the plurality of simultaneously produced sensors 15a are typically formed and bonded over cavities 11 by the following procedure, which is described with reference to FIG. 5.

The diaphragms 10 covering cavities 11 of sensors 15a are formed, for example, from a silicon wafer 3 inches in diameter, about 0.018 inches thick, and etch stopped with $10^{20}$ boron atoms/cm$^3$ at a depth of 20 microns, as sold by Spire Corporation, Bedford, Mass. 01730. Thus, the silicon wafer comprises an etch stopped layer 20 microns thick supported by a silicon substrate of much greater thickness.

In the bonding procedure, first the etch stopped side of the silicon wafer has a layer of silicon dioxide about 200 Angstroms thick formed on it by baking the silicon wafer in an oven at 900° C. for one hour, in order to increase the subsequent adhesion of the glass wafer in which the cavities 11 have been etched, as described below. Next, the silicon and glass wafers, which have been prepared as previously described, are cleaned with warm soapy water, further cleaned in an ultrasound bath for about 15 minutes, rinsed with water, rinsed with alcohol, cleaned with alcohol, rinsed with alcohol and finally air dried. The etch stopped layer of the silicon wafer is then placed on and aligned with the surface of the glass wafer which bears the cavities 11 to form a silicon and glass wafer sandwich.

The prepared silicon and glass wafers are bonded together as follows. They are first placed in a conventional vacuum chamber with a positive electrode in electrical contact with the outer surface of the silicon wafer and a negative electrode in electrical contact with the outer surface of the glass wafer. Thereafter the vacuum chamber is evacuated to about $6 \times 10^{-6}$ torr for 1 hour.

The silicon and glass wafer sandwich is then heated by a heater in the vacuum chamber to, and maintained at, 500° C. while the assembly is at this temperature, a bonding voltage is applied to the positive and negative electrodes. The bonding voltage is ramped from 0-800 VDC, maintained at 800 VC for about 8-10 minutes until the bonding current is stabilized, and then turned off. At this time the silicon and glass wafers are now bonded together with a fluid tight seal, the silicon dioxide layer on the silicon wafer aiding in the bonding process.

The temperature of the silicon and glass wafer sandwich after bonding is maintained at 500° C. for one-half hour to activate getter rings 42 in the bottoms 18 of cavities 11. As will be described below, the function of the getter rings is to remove any residual gasses or subsequent outgassing in cavities 11 after the bonding of the silicon and glass wafer 11. sandwich, thereby producing a very good vacuum in cavities Next the heater in the vacuum chamber is turned off and when the silicon and glass wafer sandwich has cooled to about 300° C., the vacuum in the vacuum chamber is released. The bonded silicon and glass wafer sandwich is removed from the vacuum chamber when it has cooled to about 200° C.

Thereupon 70% to 80% of the thickness of the silicon substrate of the silicon wafer in the bonded silicon and glass wafer sandwich is removed by mechanical polishing. Next an EDP etchant solution is prepared composed of 8 ml water, 17 ml ethylenediamine, and 3 g pyrocatechol. The EDP etchant solution is heated to approximately 115° C. and used to chemically etch the pure silicon substrate away, leaving only its etch stopped layer, about 20 microns thick, which is bonded to the glass wafer and which forms diaphragms 10 covering cavities 11. The 20 microns thickness is determined by periodically checking the thickness of the silicon remaining during the etching process, such as by measuring light transmission through the silicon.

When pressure is the physical parameter which the first embodiment 15a of the spectral modulation sensor 15a is designed to monitor, it is preferred that cavity 11 be evacuated. This provides for an optically resonant sensor 15a relatively immune to errors that would otherwise arise due to changes in temperature if cavity 11 contained some media which significantly expanded or contracted in response to changes in temperature. If a differential pressure sensor 15a is desired, cavity 11 need not be evacuated.

Although there are many ways in which the cavity 11 can be evacuated, it is preferred to use a getter structure in the form of a ring 42 of deposited layers of chrome and iron in the bottom of each cavity 11 to absorb residual gasses or subsequent outgassing in cavity 11 after the initial evacuation of cavity 11 is performed.

The getter rings for cavities 11 in the glass wafer are prepared as follows. First, the glass wafer which has been prepared as described above, is baked at 125° C. for ½ hour.

Then using conventional techniques, a second photographic mask is prepared having an array of donut shaped masks. Since the cavities 11 are 350 microns in diameter, for example, the corresponding donut shaped mask for each cavity 11 would have an inner diameter of 230 microns and an outer diameter of 330 microns, for example.

Then, the donut shaped masks on the second photographic mask are aligned with the cavities 11 in the glass wafer; and the mask and glass wafer assembly is exposed, as before. The glass wafer is then, as before, developed and rinsed; and then bakedat 90° C. for ½ hour. This leaves an unprotected donut shaped hole in the photoresist in the bottom 18 of each cavity 11 having an inner diameter of 230 microns and an outer diameter of 230 microns.

Next, using conventional vacuum deposition techniques, a layer of chrome 200 Angstroms thick is deposited on the entire glass wafer, followed by a layer of iron 800 Angstroms thick being deposited on the layer of chrome. The chrome helps the iron, which is the actual getter material, to adhere to the glass wafer. Then the glass wafer is placed in acetone and agitated with ultrasound. This removes the remaining photoresist and also removes the chrome and iron, but only the chrome and iron which was over said remaining portions of photoresist. Finally, the glass wafer is washed with detergent; rinsed with water; and dried.

The getter structure thus left will comprise a donut shaped ring of the deposited chrome and iron layers with an inner diameter of 230 microns and an outer diameter of 330 microns centered in the bottom 18 of each cavity 11 to fit around the stop rings in the area on the bottom of the cavity that is not needed for optical function.

It is desirable to set the height of raised annular stop ring 40 relative to bottom surface 18 of cavity 11 with an accuracy of about plus or minus 1% of the light source's central wavelength. As an example, for a light source operating at 850 nm, a placement accuracy of 85 Angstroms is indicated—a very small error in height. The manufacture of sensors with this tight a dimensional tolerance in high yield is difficult.

The correct stop ring height may be obtained by careful differential etching of the inner cavity and surrounding ring; or, it may be generated at a later time by a deformation process. The deformation process is described herein.

Most materials show a combination of elastic and plastic response to loading at elevated temperatures. In this condition, when a load is applied to an object and then removed, the object only partially recovers its original shape. A protocol has been developed for setting the height or stop ring 40 using this phenomena.

The stop ring height is initially defined by standard etching methods so that it is slightly higher than the final desired value, while overall cavity depth is set to a value deeper than desired for standard operation by a distance which corresponds with one to two resonance cycles of the sensor's periodic response function.

The sensor with these internal dimensions is then placed on a special heated surface. The surface has an optical fiber flush-mounted in it that is positioned under the sensor center to provide continuous monitoring of the deformation process.

A steady and uniform load is applied to diaphragm 10. Through an earlier trial-and-error process, this optimum loading has been determined such that diaphragm 10 contacts and loads stop ring 40. The degree of loading and application time are such that when the load is removed, the stop ring rebounds to the desired final position. In practice, during loading the diaphragm moves to a depth corresponding with the spectral ratio value indicated by point C on the response function curve in FIG. 4. When the loading is removed, the stop ring rebounds to a height corresponding with a value below point C in FIG. 4. The object of the trial-and-error process is to load the ring so that after the load is removed, the final stop ring height during actual operation of the sensor approximately corresponds with position B on the response function curve in FIG. 4 (i.e., ring contact point E on the response function curve in FIG. 6).

Concurrently, the cavity walls rebound to a height such that the spectral ratio detected when the diaphragm is in its undeformed state corresponds with position D on the response function curve in FIG. 4. The range of standard operation of the sensor after this loading operation corresponds with the spectral ratio values between points D and B in FIG. 4. Through this set of steps, both the stop ring height and initial operating point of the sensor with the diaphragm in the undeformed state can be set.

Setting the initial operating point and stop ring height in one step is efficient but requires some skill. An alternative second approach can be used that performs these steps individually. In this approach, a portion of raised annular stop ring 40 is made of a material that has substantially no mechanical strength at elevated temperature. Materials that may be used include any metal at a temperature slightly below its melting point, or a meltable material such as silicon-gold eutectic or indium-based solder, processed slightly above its melting point.

The stop ring height is set by heating sensor 15a to the appropriate softening temperature and then applying a mechanical or pressure load to diaphragm 10 so that the diaphragm contacts the softened or molten stop material. The temperature is then reduced to ambient while maintaining load. When the load is released, the diaphragm springs away from the stop ring and is free to flex in response to pressure. In this process it is apparent that the stop ring material is chosen to be much less rigid at temperature than the sensor substrate.

The present invention is not limited in its operation to sensors designed to monitor pressure. For example, the inventive sensor with increased monotonic range can be used with sensors designed to measure the concentration and/or presence of chemical species such as pH, $pO_2$, $pCO_2$, certain ions etc. Such sensors are designed with sensitive media positioned in the cavity of the sensor, and the sensitive media swells in response to the concentration and/or presence of these chemical species. Such sensors without the invention are described at col. 22, line 39 to col. 24, line 16 of U.S. Pat. No. 4,678,904 which is assigned to the assignee of the present invention, and which is incorporated herein by reference.

Various additional modifications and adaptations of the invention will become apparent to those skilled in the art. All such variations of these teachings through which the invention has advanced the art are properly considered within the spirit and scope of the invention.

What is claimed is:

1. A variable gap optical sensor device with a periodic response function comprising:
    a pair of opposed reflective surfaces, at least a first one of said surfaces being integral with a flexible diaphragm so that the gap width between the reflective surfaces can be varied, the gap in the undeformed state being no greater than 30 μm;
    an optical fiber mounted with respect to said opposed reflective surfaces so that light from the core of said fiber will be incident on at least a portion of said surfaces, and light reflected from said surfaces will be incident on said core; and
    stiffening means comprising an optically transmissive raised stop means intermediate said opposed reflective surfaces, whereby the potential variation in said gap width is diminished, thereby increasing the monotonic range of said periodic response function.

2. The optical sensor device of claim 1 wherein said stiffening means comprises a raised stop ring defining an aperture through which said incident light and said reflected light are transmitted.

3. The optical sensor device of claim 2 wherein said raised stop ring is mounted opposite said first surface, and said first surface comes into contact with said stop ring during operation of said sensor device, thereby diminishing the potential variation in gap width and increasing the monotonic range of said periodic response function.

4. The optical sensor device of claim 3 wherein the height of said raised stop ring is selected to coincide with a gap width corresponding with an output of said periodic response function within its monotonic range, and wherein the flexibility of said flexible surface is decreased upon contact with said raised stop ring, thereby increasing the period of said periodic response function and creating a dual stage periodic response function with increased monotonic range.

5. The optical sensor device of claim 4 wherein said selected height of said stop ring is such that the second stage of said dual stage periodic response function begins at approximately 85 percent of the end of the monotonic region of the first stage of said periodic response function.

6. The optical sensor device of claim 4 wherein said flexible diaphragm comprises a bowing diaphragm, the other opposed reflective surface is included in a body defining a cavity, said optical fiber is mounted to the outside of said body, said bowing diaphragm is mounted to form a cover for said cavity, and said raised stop ring is within said cavity.

7. The optical sensor device of claim 4 wherein said raised stop ring and said first surface are formed of different materials such that the height of said raised stop ring may be adjusted during manufacture by contacting the stop ring with the first surface to deform the stop ring by loading without substantial deformation of said first surface.

8. The optical sensor device of claim 4 wherein said raised stop ring and said first surface are formed of different materials such that the height of said raised stop ring may be adjusted during manufacture by heating the sensor device to the softening temperature of the stop ring and contacting the stop ring with the first surface to deform the softened stop material without substantial deformation of said first surface.

9. The optical sensor device of claim 1 wherein said stiffening means comprises a transparent stop media intermediate said opposed reflective surfaces.

10. In an optically resonant sensor comprising a pair of opposed reflective surfaces, one of which is integral with a bowing diaphragm having a first radius, and having a periodic response function, the improvement comprising:
    stiffening means comprising a raised stop means opposite said bowing diaphragm whereby a second effective radius results during operation of the sensor to provide a second stage of said response function with increased period, and whereby the operating range in which said response function is monotonic is increased.

11. The optically resonant sensor of claim 10 further comprising supporting means at the periphery of said first reflective surface, wherein said stiffening means comprises a raised stop ring defining an aperture intermediate said supporting means.

12. The optically resonant sensor of claim 11 wherein the height of said raised stop ring is selected to coincide with the distance between said opposed reflective surfaces that corresponds with a value of said periodic response that is within the monotonic range of said periodic response in which the sensor is designed to operate.

13. The optically resonant sensor of claim 12 wherein said selected height is such that said location is approximately 85 percent of the total of said monotonic range.

14. The optically resonant sensor of claim 12 wherein the parameter measured by the sensor is pressure.

15. The optically resonant sensor of claim 12 wherein the parameter measured by the sensor is the concentration of a chemical species and wherein a sensitive media is disposed between said opposed reflective surfaces.

16. The optically resonant sensor of claim 10 wherein said stiffening means comprises transparent stop media between said opposed reflective surfaces.

17. The optically resonant sensor of claim 16 wherein the height of said raised transparent stop media is selected to coincide with the distance between said opposed reflective surfaces that corresponds with a value of said periodic response function that is within the monotonic range of said periodic response in which the sensor is designed to operate.

18. The optically resonant sensor of claim 17 wherein said selected height is such that said location is approximately 85 percent of the total monotonic range.

19. An optically resonant sensor device with a pair of opposed reflective surfaces which are interrogated with light to generate a response function that varies periodically as the distance between the opposed reflective surfaces varies monotonically in response to the parameter being sensed, wherein:
   a first one of said reflective surfaces comprises a bowing diaphragm, and the distance between the opposed reflective surfaces corresponds with the value of the parameter being monitored by the sensor;
   during operation of the sensor, there is a range of distances between said opposed reflective surfaces which corresponds with a selected monotonic region of a first stage of said periodic responce function in which there is a unique one-to-one relation between the values of the response function and the monotonically varying distance between said opposed reflective surfaces; and
   said sensor device further comprises raised stop means for altering the period of said periodic response function to increase the range of said distances in which said response function is periodic thereby creating a dual stage monotonic sensor response.

20. The sensor device of claim 19 wherein said raised stop means comprises a raised annular stop ring opposite said first reflective surface, and said raised stop ring comes into contact with said first reflective surface within said range of distances corresponding with a monotonic region of said periodic response function, thereby stiffening said first reflective surface and creating a second stage of said response function with a period greater than that of the first stage.

21. The sensor device of claim 20 wherein the height of said raised annular stop ring is selected such that the second stage of said response function begins at a value corresponding with approximately 85 percent of the selected monotonic region of said periodic response function.

22. The sensor device of claim 20 wherein the second opposed reflective surface is included in a body defining a cavity, said bowing diaphragm is mounted to form a cover for said cavity, and said raised annular stop ring is within said cavity.

23. The sensor device of claim 20 wherein said raised annular stop ring and said first reflective surface are formed of different materials such that the height of said raised stop ring may be adjusted during manufacture by contacting the stop ring with said first reflective surface to deform the stop ring by loading without substantial deformation of said first reflective surface.

24. The sensor device of claim 20 wherein said raised annular stop ring and said first reflective surface are formed of different materials such that the height of said raised stop ring may be adjusted during manufacture by heating the sensor device to the softening temperature of the stop ring and contacting the stop ring with said first reflective surface to deform the softened material without substantial deformation of said first reflective surface.

25. The sensor device of claim 19 wherein the parameter being measured is pressure.

26. The sensor device of claim 19 wherein said limiting means comprises a transparent stop media intermediate said opposed reflective surfaces.

* * * * *

UNITED STATES PATENT AND TRADEMARK OFFICE
CERTIFICATE OF CORRECTION

PATENT NO. : 4,983,824
DATED : January 8, 1991
INVENTOR(S) : Elric W. Saaski and Dale M. Lawrence It is certified that error appears in the above-identified patent and that said Letters Patent is hereby corrected as shown below:

Column 1, line 67 "periodic the" should read -- periodic: the --

Column 3, line 40 "secondembodiment" should read
-- second embodiment --

Column 10, line 43 "load the ring" should read -- load the stop ring --

Signed and Sealed this

Twenty-eighth Day of July, 1992

Attest:

DOUGLAS B. COMER

*Attesting Officer*    *Acting Commissioner of Patents and Trademarks*